(12) United States Patent
Winiski et al.

(10) Patent No.: US 9,914,906 B2
(45) Date of Patent: Mar. 13, 2018

(54) PROCESS FOR SOLID-STATE CULTIVATION OF MYCELIUM ON A LIGNOCELLULOSE SUBSTRATE

(71) Applicants: Jacob Winiski, Troy, NY (US); Sue Van Hook, Cambridge, NY (US); Matthew Lucht, Troy, NY (US); Gavin McIntyre, Troy, NY (US)

(72) Inventors: Jacob Winiski, Troy, NY (US); Sue Van Hook, Cambridge, NY (US); Matthew Lucht, Troy, NY (US); Gavin McIntyre, Troy, NY (US)

(73) Assignee: Ecovative Design LLC, Green Island, NY (US)

( * ) Notice: Subject to any disclaimer, the term of this patent is extended or adjusted under 35 U.S.C. 154(b) by 0 days.

(21) Appl. No.: 15/064,944

(22) Filed: Mar. 9, 2016

(65) Prior Publication Data

US 2016/0264926 A1 Sep. 15, 2016

Related U.S. Application Data

(60) Provisional application No. 62/132,578, filed on Mar. 13, 2015.

(51) Int. Cl.
  *C12N 1/14* (2006.01)
  *C12N 1/22* (2006.01)
(52) U.S. Cl.
  CPC ............... *C12N 1/14* (2013.01); *C12N 1/22* (2013.01)
(58) Field of Classification Search
  None
  See application file for complete search history.

(56) References Cited

U.S. PATENT DOCUMENTS

| | | | | |
|---|---|---|---|---|
| 2008/0295399 | A1* | 12/2008 | Kawai | A01G 1/04 47/1.1 |
| 2012/0315687 | A1* | 12/2012 | Bayer | C12N 1/14 435/254.1 |
| 2015/0038619 | A1* | 2/2015 | McIntyre | B27N 3/002 524/13 |

OTHER PUBLICATIONS

Goodell et al., "Fungal Decay of Wood: Soft Rot-Brown Rot-White Rot", In Development of Commercial Wood Preservatives; Schultz et al., Ed. ACS Symposium Series; American Chemical Society: Washington, DC, 2008, pp. 9-31.*

* cited by examiner

*Primary Examiner* — Michelle F. Paguio Frising
(74) *Attorney, Agent, or Firm* — Francis C. Hand; Carella, Byrne, et al.

(57) ABSTRACT

In one embodiment, the process combines a fraction (up to 15%) of a lignocellulose substrate with supplemental nutritional material and hydrates the fraction to a moisture content of from 40% to 70% by weight. The hydrated substrate fraction is heat processed to remove ambient bioburden (yeast, mold, bacteria) and to maintain the hydrated substrate fraction in an aseptic condition. Thereafter, the hydrated substrate fraction is inoculated with a fungus and incubated to obtain a myceliated substrate which is then reduced into discrete particles. The remaining fraction of the substrate is combined with water and then combined with the discrete particles of myceliated substrate and incubated to obtain a second myceliated substrate which is then reduced into discrete particles. The second myceliated substrate is combined with supplemental nutritional material and incubated to obtain a third myceliated substrate composed of at least 10% mycelium.

14 Claims, 4 Drawing Sheets

PROCESS FOR SOLID-STATE CULTIVATION OF MYCELIUM ON A LIGNOCELLULOSE SUBSTRATE

This application claims the benefit of Provisional Patent Application 62/132,578, filed Mar. 13, 2015

This invention relates to a process for solid-state cultivation of mycelium on a lignocellulose substrate.

BACKGROUND

Conifer trees (Pinophyta, or softwoods) are cone-bearing gymnosperm species. Conifer species are particularly characterized by production of resin containing a high concentration of terpenes, especially as compared to hardwood species. This resin is considered one of the oldest and most important non-wood products derived from conifer trees, which is used to produce a number of products including turpentine and rosin. Many of the monoterpenoids that make up the terpene fraction of conifer resin are known to be highly inhibitory to the growth of wood decomposing fungi, including alpha-pinene, beta-pinene, limonene, camphene, and myrcen]. The inhibitory activity of conifer terpenes on wood decomposing fungi functions as a natural defense against fungal infection. As a result, wood decomposing fungi are typically characterized by their occurrence on either hardwood and/or conifer wood species, governed in part by varying levels of tolerance to conifer terpenes.

Solid-state cultivation of fungi on organic matter typically requires heat sterilization/pasteurization in order to eliminate/reduce ambient bioburden (yeast, mold, bacteria) present in the given substrate. This bioburden, if not eliminated prior to inoculation with the fungus species, will compete with the fungus for nutrition leading to partial or total inhibition of mycelium production. Additionally, most fungus cultivation procedures require that incubation occur in an aseptic arena to prevent accidental introduction of contaminant species post-sterilization/pasteurization (i.e. aseptic cultivation).

In the mushroom cultivation industry, the use of conifer substrates is largely avoided. This is due to two factors, the first being terpene inhibition as described above. Secondly, conifer wood provides poor nutrition for supporting rapid fungal growth, with specific deficiencies in nitrogen and trace minerals. Commercial cultivation of mushrooms on conifer substrates is rare, and often utilizes tree species with low resin content (such as Douglas Fir) blended 1:1 with non-conifer substrates (hardwood, agricultural waste) and high-value supplemental nutrition (wheat bran, brown rice flour) within cultivation systems that require aseptic cultivation as described above. Though in practice the use of conifer substrates for mushroom cultivation is rare, there are a multitude of patents, including U.S. Pat. No. 7,984,584, indicating the use of conifer substrates for mushroom cultivation, particularly for shimenji mushroom production. In this case, typical supplementation rates with non-conifer species and high value nutrition are 50 to >60%.

Accordingly, it is an object of the invention to provide an economically feasible process for solid-state cultivation of mycelium on a lignocellulose substrate.

It is another object of the invention to reduce the cost of processing mycelium on a lignocellulose substrate.

It is another object of the invention to provide a mycelium-based biomaterial for use in the engineered wood industry.

Briefly, the invention provides a solid-state process wherein mycelium is cultivated on a lignocellulose substrate and, particularly, a conifer/gymnospermous substrate.

The process leverages the inhibitory nature of conifer and terpene containing substrates, in concert with specific fungal strain selection criteria and sequence of mycelium expansion and nutrition supplementation, to reduce the need for aseptic cultivation procedures to a maximum of 15% of the total mass of substrate being myceliated.

The process proposes a maximum supplemental nutrition rate of 14%, which significantly reduces cost as compared to other patents in the field of mushroom cultivation. Further, the methodology employed leverages a very specific sequence of staged mycelium expansion and rationed nutritional supplementation that selects for a desired fungal species over that of contaminant organisms (mold, bacteria, yeast). Within this process, the total mass requiring heat-processing and aseptic control is reduced to a maximum of 15% which provides for unique processing efficiency as compared to the current state of the art of mushroom cultivation.

In the context of manufacturing a biomaterial by growing mycelium on a solid substrate, a primary cost driver is processing time (growth time), which is governed by the rate at which the fungus expands (grows) through the solid substrate. When presented with the problem of growing mycelium on a conifer substrate, the most obvious assumption would be to utilize fungus species that occur exclusively on conifer trees in nature. Research found the opposite to be true; in trials conducted with a multitude of fungal and conifer wood species, it was found that fungal species which primarily colonize hardwoods in nature, and are tolerant of the terpene-containing fraction of the conifer substrate, had expansion rates (the rate at which the mycelium grows through the given substrate) 55%-61% faster than species that occur on conifers exclusively. As a result, this study indicated that the most attractive species in regard to processing time are those that meet the criteria described in process step 1 below. Additionally, the increase in the rate of expansion associated with the selection criteria of 1 was found to be critical for successful exclusion of contaminant organisms; therefore the specific combination of fungal strain selection, substrate species selection, and the specific sequence in which the fungus is expanded in concert with introduction of supplemental nutrition described in the proposed process is critical for achieving both the desired processing efficiency and material performance.

There are several patented and common processes oriented toward growing mycelium on non-sterilized wood substrate without maintaining aseptic control (i.e. non-aseptic cultivation). These processes differ in important and significant ways from the proposed process in both methodology, result, and application as detailed below:

1. Log mushroom cultivation: It is common mushroom cultivation practice to inoculate intact hardwood logs for the purposes of outdoor mushroom cultivation. This process is dependent on using intact logs, specifically leveraging the bark along with added wax to exclude contaminant organisms. Therefore, the process is not applicable to particulate substrates. Additionally, this process specifically teaches not to use logs from softwoods in most scenarios, requires processing times often exceeding 1 year, and does not produce adequate biomass for material applications.

2. Biopulping: This process teaches the utilization of white rot fungi to degrade lignin in wood chips prior to mechanical pulping in the paper manufacturing industry, thereby reducing the energy required to effectively pulp the chips. The biopulping process does not require aseptic incubation conditions, but is also not specifically concerned with exclusion of other fungi/mold species as the proposed process is. Additionally, this process requires heat disinfection of the entire mass of substrate being processed, whereas the proposed process only heat disinfects a maximum of 15% of the wood particles processed. Furthermore, the specific fungal strains utilized in biopulping as demonstrated in testing performed at Ecovative do not perform adequately as a bioresin, whereas the strain selection criteria detailed here selects for species which do perform adequately as a bioresin.

3. Cartapip97]: The product Cartapip97 is intended for inoculating particulate conifer and hardwood substrates without sterilization or aseptic control. Similar to biopulping this product is designed to effect a specific effect on the wood substrate rather than accumulate fungal biomass; the only application is to reduce the effect of sapstain fungi on wood particles and logs. The proposed methodology specifically teaches the negotiation of supplemental nutrition relative to fungal expansion to (a) exclude contaminant organisms, (b) accumulate at least 10% fungal biomass, and (c) utilize fungal species with morphological characteristics that provide value as a bioresin. Cartapip97 does not leverage supplemental nutrition for biomass accumulation and only teaches to a specific effect on substrate with a specific fungal species, not to the functionality of the biomass itself as a material.

In accordance with the process of the invention, after obtaining a lignocellulose substrate, a fraction of the substrate of up to 15% is combined with supplemental nutritional material at a ratio of up to 14% of the dry mass of the fraction and hydrated to a moisture content of from 40% to 70% by weight.

The hydrated substrate fraction is then heat processed for a period of time sufficient to remove ambient bioburden (yeast, mold, bacteria) and to maintain the hydrated substrate fraction in an aseptic condition.

Thereafter, the hydrated substrate fraction is inoculated with a fungus and incubated for a period of time to allow the fungus to grow hyphae and to allow the hyphae to form a network of interconnected mycelia cells through and around discrete particles of the substrate fraction to obtain a myceliated substrate.

Next, the myceliated substrate is reduced into discrete particles, for example, by agitation, grinding or otherwise.

The remaining fraction of the substrate is then combined with water to obtain a moisture content of 40% to 70%; then combined with the discrete particles of myceliated substrate; and incubated for a period of time to allow the fungus in the discrete particles of the myceliated substrate to grow hyphae and to allow the hyphae to form a network of interconnected mycelia cells through and around discrete particles of the remaining fraction of the substrate to obtain a second myceliated substrate.

The second myceliated substrate is then reduced into discrete particles; combined with supplemental nutritional material at a ratio of up to 14% of the dry mass of the second myceliated substrate; and incubated for a period of time to allow the fungus in the discrete particles of myceliated substrate to grow hyphae and to allow the hyphae to form a network of interconnected mycelia cells through and around discrete particles of the remaining fraction of the substrate to obtain a third myceliated substrate composed of at least 10% mycelium.

BRIEF DESCRIPTION OF THE DRAWINGS

These and other objects and advantages of the invention will become more apparent from the following detailed description taken in conjunction with the accompanying drawings wherein.

DETAILED DESCRIPTION OF THE INVENTION

Figure 1:
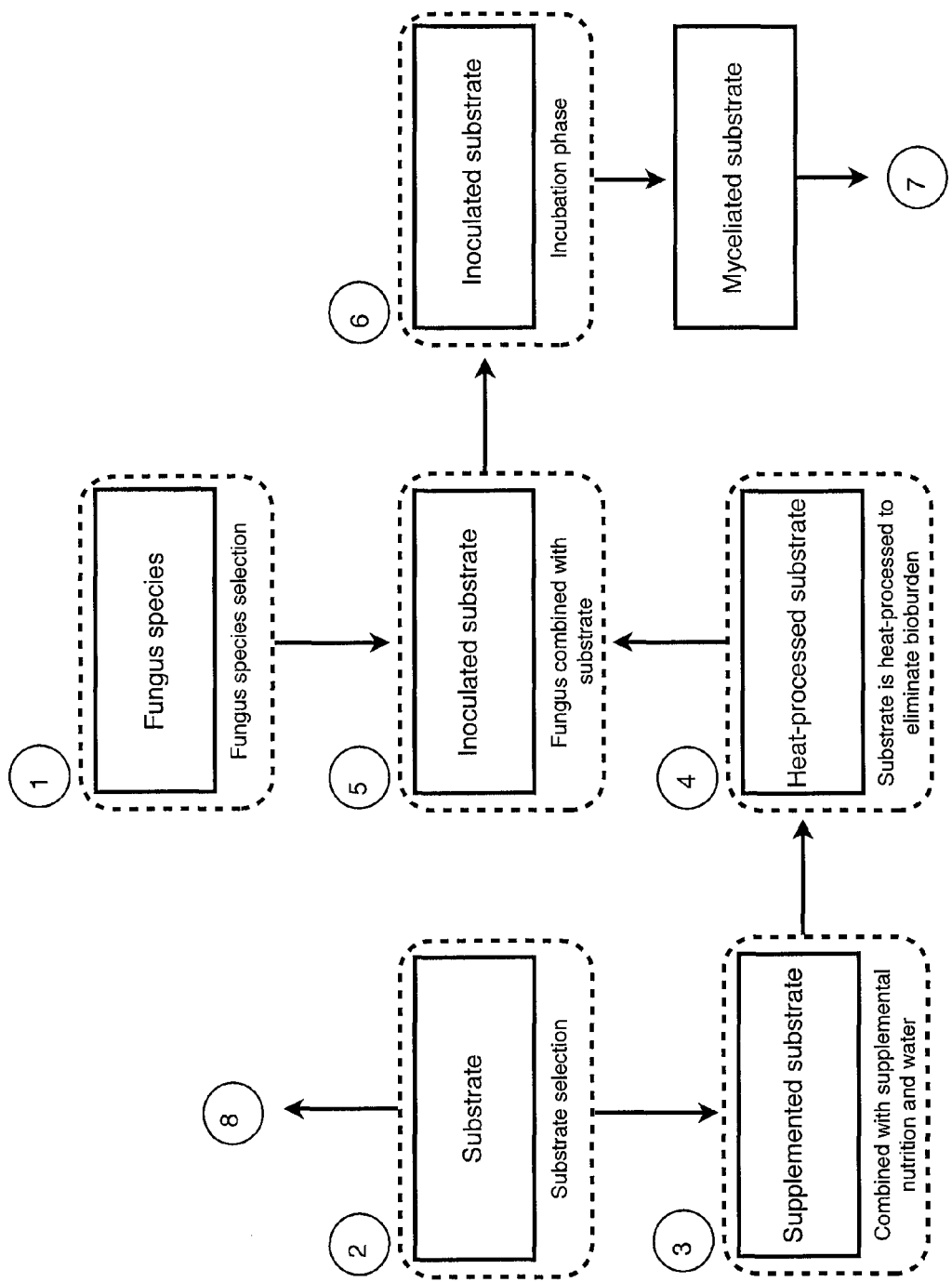
FIG. 1 schematically illustrates a flow diagram of the initial steps of the process of the invention.

Referring to FIG. 1, the process for solid-state cultivation of mycelium is carried out on a lignocellulose substrate, such as a conifer/gymnospermous substrate or a non-conifer terpene-containing substrate, without heat disinfection or aseptic control for application as a bioresin.

In step 1 of the process, a fungus species is selected according to the following criteria:
 a. The species is a member of the Basidiomycetes, Ascomycetes or Zygomycetes
 b. The species is a saprophytic white rot, brown rot, or soft rot.
 c. The species occurs in mixed environments of both deciduous and conifer wood.
 d. The species occurs on both angiosperms and gymnosperms.
 e. The species is adequately tolerant of the monoterpene content associated with substrates containing up to 25% resin (w:w) as indicated by mycelium expansion on the given substrate at an average rate of at least 16 mm per day.
 f. The species produces cellular components which serve a structural capacity.
 g. The structural cellular components of f are comprised of thick-walled cells such as skeletal hyphae or pseudoparenchymal cells.

In step 2 of the process, a substrate is obtained according to any combination of the following criteria:
 a. The substrate is comprised entirely of gymnosperm wood.
 b. The substrate is between 50% and 100% gymnosperm wood blended with other plant matter.
 c. The gymnosperm fraction is comprised of a single wood species.
 d. The gymnosperm fraction is comprised of multiple wood species.
 e. The gymnosperm fraction retains it's native resin and monoterpene content
 f. The substrate is of any of a-e with additional terpene supplemented in addition to the native terpene content.
 g. The substrate is a lignocellulose plant matter not derived from a gymnosperm tree species supplemented with terpene.

The substrate is typically in the form of particles or fibers and may encompass any number of particle sizes, including wood chips, and aspect ratios.

In step 3 of the process, up to 15% of the total mass of the substrate of step 2 is combined with supplemental nutritional material in the form of starch, simple sugars, lipids, and trace minerals at a rate of up to 14% of the dry mass of the substrate and moistened with water to a moisture content of 40-70%.

In step 4 of the process, the substrate of step 3 is heat-processed for a period of time sufficient to eliminate the ambient bioburden and maintained in aseptic conditions.

In step 5 of the process, the heat-processed substrate of step 4 is inoculated with the fungus of step 1.

In step 6 of the process, the inoculated substrate of step 5 is incubated under aseptic conditions for a period of time until the fungus has expanded around and throughout the discrete particles of substrate (i.e. the substrate is myceliated by the fungus). During this time, the fungus grows hyphae that form a network of interconnected mycelia cells through and around discrete particles of the substrate fraction to obtain a myceliated substrate.

Figure 2:
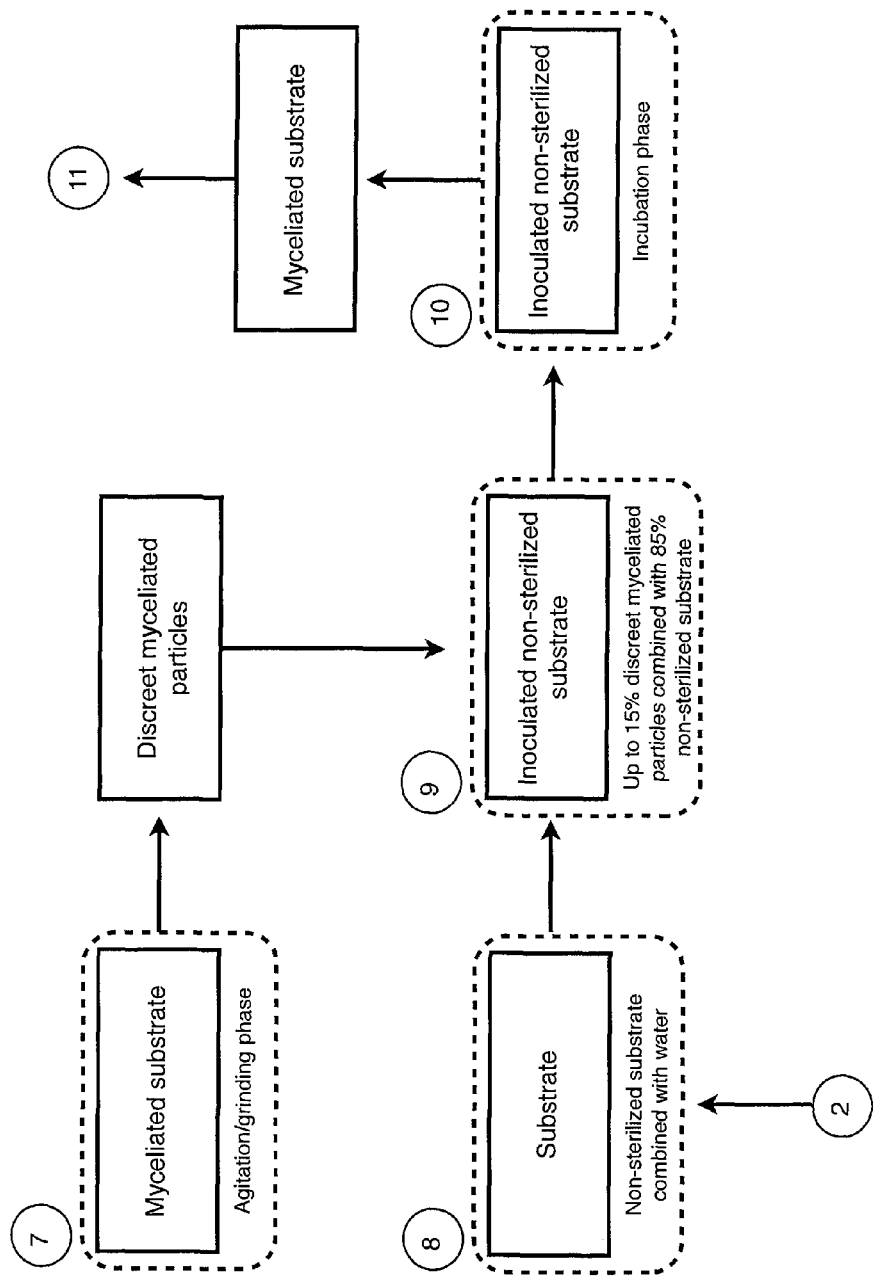
FIG. 2 schematically illustrates a flow diagram of the subsequent steps of the process of the invention.

Referring to FIG. 2, in step 7 of the process, the myceliated substrate obtained in step 6 is reduced into discrete particles, e.g. by being agitated, ground, or otherwise reduced.

In step 8 of the process, the remaining non-sterilized fraction of the substrate of step 2 is combined with water to a moisture content of 40-70% without heat-processing or any other treatment intended to reduce the ambient bioburden of the substrate.

In step 9 of the process, the moistened substrate of step 8 is combined with the discrete, myceliated particles of step 7 at a rate of up to 15% of the total dry mass. There is no supplemental starch, simple sugars, lipids, or trace minerals supplemented at this stage.

In step 10 of the process, the substrate of step 9 is incubated in a static mass without aseptic controls, while maintaining moisture content, for a period of 4 to 10 days until the fungus present on the particles of step 7 expands between and around the particles of the substrate of step 8 (i.e. the substrate is myceliated by the fungus). During this time, the inoculated mass is incubated for a period of time to allow the fungus in the discrete particles of myceliated substrate to grow hyphae and to form a network of interconnected mycelia cells through and around discrete particles of the remaining fraction of the substrate to obtain a second myceliated substrate.

Figure 3:
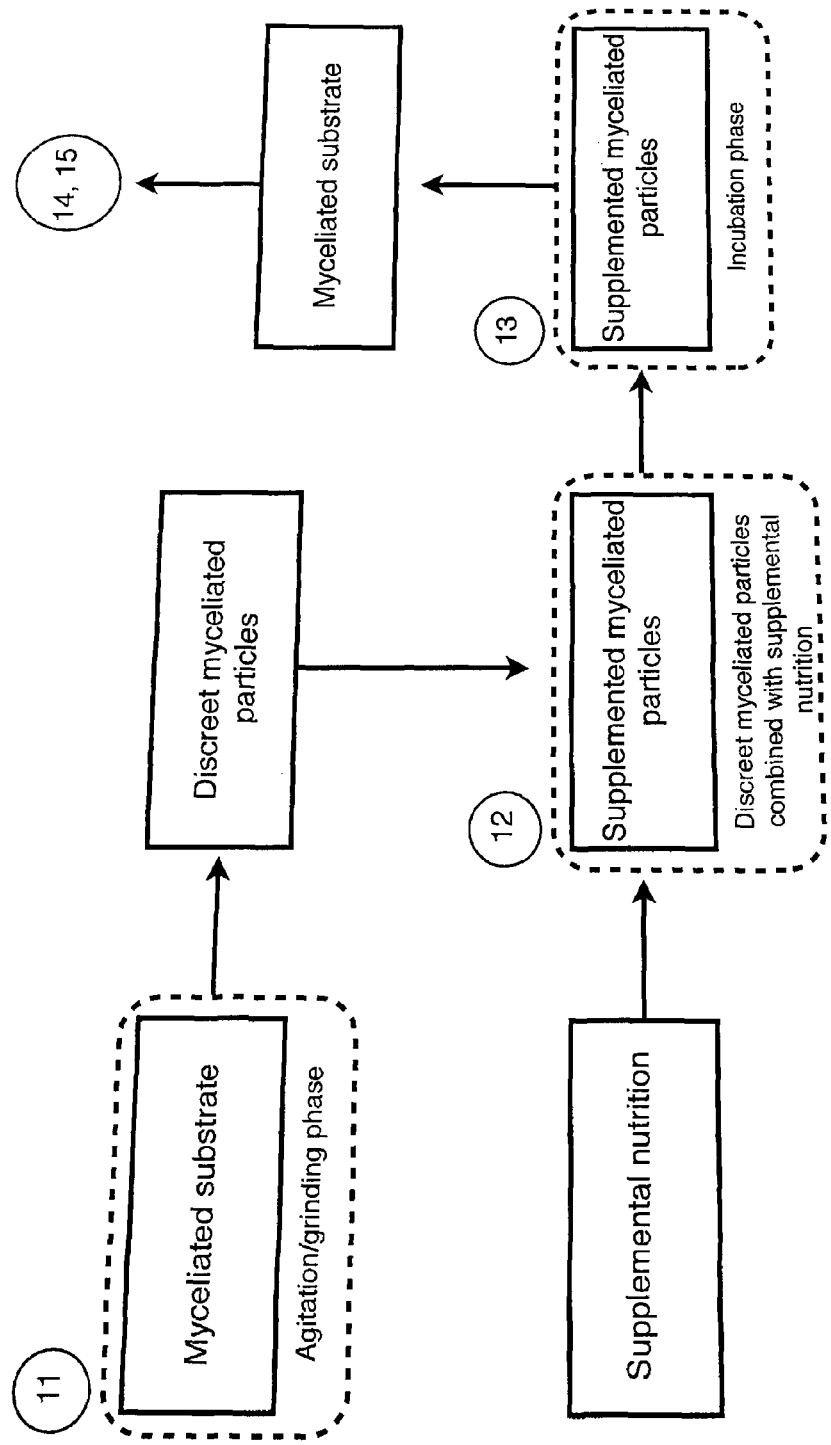
FIG. 3 schematically illustrates a flow diagram of further subsequent steps of the process of the invention.
Figure 4:
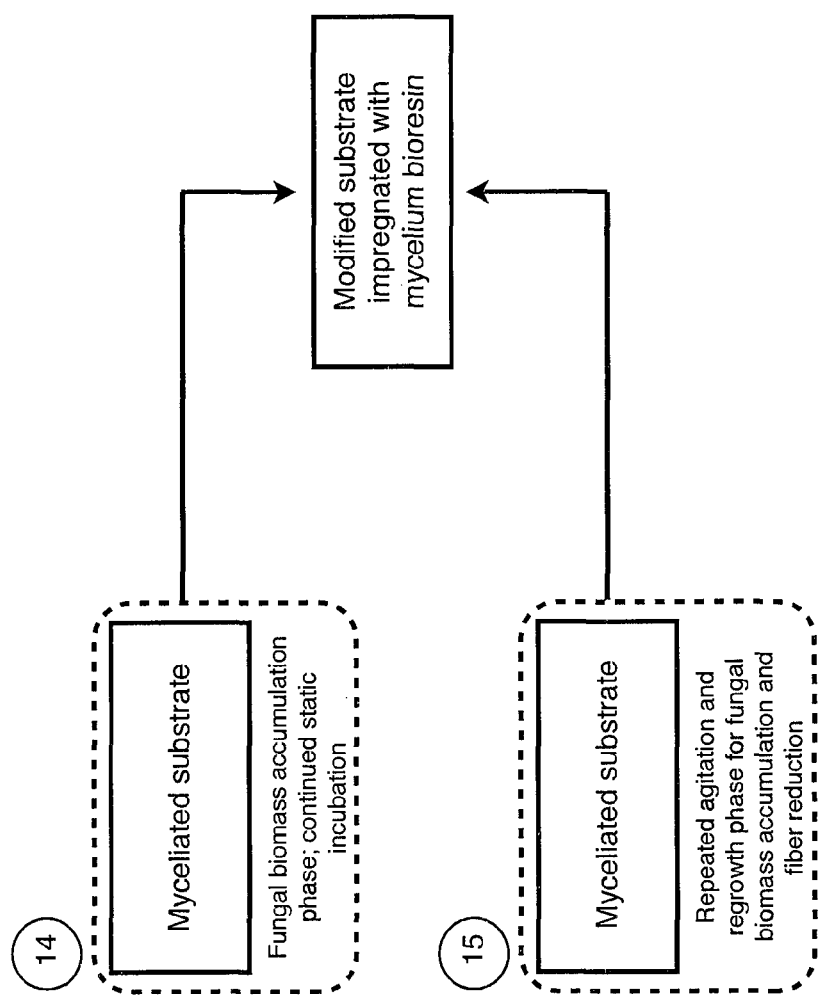
FIG. 4 schematically illustrates a flow diagram of the final optional steps of the process of the invention

Referring to FIG. 3, in step 11 of the process, the myceliated substrate obtained in step 10 is reduced into discrete particles, e.g. by being agitated, ground, or otherwise reduced.

In step 12 of the process, the discrete particles of the second myceliated substrate of step 11 are combined with supplemental nutritional material at a ratio of up to 14% of the dry mass of the second myceliated substrate according to the below criteria:
  a. Up to 22% of supplemental nutrition may be calcium
  b. Up to 38% of the supplemental nutrition may contain at least 50% starch, 20% protein, and 2% fat
  c. Up to 38% of the supplemental nutrition may contain at least 3% starch, 12% simple sugars, 8% crude fat, 0.3% calcium, 2% potassium, 200 ppm iron, 60 ppm zinc, and 40 ppm manganese
  d. Up to 66% of the supplemental nutrition may contain at least 15% protein, 19% starch, 7% simple sugars, 4% fat, 0.1% calcium, 1% phosphorus, 1% potassium, 100 ppm iron, 100 ppm zinc, 100 ppm manganese, and 2% nitrogen
  e. Up to 5% of the supplemental nutrition may be potassium In step 13 of the process, the supplemented myceliated particles of step 12 are incubated once again according, to step 10 to effect "regrowth" of the fungus into a cohesive network of filamentous hyphae growing around and between the discrete particles of substrate. From this stage, processing continues to either step 14 or 15.

In step 14 of the process, the incubation stage of step 13 is continued until one or both of the below have been achieved:
  a. The total dry mass of myceliated substrate is composed of at least 10% fungal biomass to achieve functionality as a bioresin. The term "bioresin" means that the dry mass of myceliated substrate may be used for mycelium-based biomaterial applications within the engineered wood industry. In this case, the mycelium is leveraged as a resin for binding together wood particles as a direct replacement for urea-formaldehyde adhesive.
  b. Fiber components of the substrate (cellulose, hemicellulose, lignin) have been reduced by the enzymatic action of the fungus to a desired stage. Specifically, regarding engineered wood applications, the "desired stage" means that the concentrations of cellulose/hemicellulose/lignin have been reduced by the fungus in order to (1) better optimize the internal bond and flexural strength performance by increasing the porosity of the wood particle and increasing impregnation with mycelium, and/or (2) reduce the water absorption characteristics by removing a portion of the water soluble fiber components cellulose/hemicellulose. The exact extent to which these components need to be consumed/reduced by the fungus depends on application and substrate composition.

The period of time of incubation for step 14a is sufficient to allow the fungus in the discrete particles of myceliated substrate to grow hyphae and to form a network of interconnected mycelia cells through and around these discrete particles to obtain a third myceliated substrate composed of at least 10% mycelium.

In step 15 of the process, the myceliated substrate of step 13 or step 14 is agitated, ground, or otherwise reduced to discrete particles and incubated again according to step 10 to effect "regrowth".

The supplemental nutrition per step 12 may be mixed in progressively at each agitation stage. This process of agitation and regrowth is repeated as desired until one or both of the below have been achieved:
  a. The total dry mass of myceliated substrate is composed of at least 10% fungal biomass to achieve functionality as a bioresin.
  b. Fiber components of the substrate (cellulose, hemicellulose, lignin) have been reduced by the enzymatic action of the fungus to a desired stage.

The following are specific examples of the process of the invention.

Example 1: Efficient Impregnation of Lignocellulose Particles with Mycelium for Application as a Bioresin 1. A fungus species is selected per the criteria of process step 1, which may include (but not limited to): *Trametes hirsute, Trametes elegans, Trametes gibbosa, Trametes versicolor, Stereum ostrea, Stereum hirsutum, Trichaptum biforme, Xylaria polymorpha, Xylaria hypoxylon, Kretz-*

*schmaria deusta, Schizophyllum commune, Phellinus gilvus, Phanerochaete* spp., *Ganoderma* spp., *Trichoderma* spp., *Pleurotus* spp.
2. A substrate is selected per the criteria of process step 2, which may include (but not limited to):
   a. Conifer wood combined with 50%-0% hardwood. The conifer fraction may be Jack Pine, Red Pine, Lodgepole pine, spruce, or fir. The hardwood fraction may be maple, birch, alder, ash, oak, or poplar.
   b. 100% conifer wood comprised of a single or multiple species including Jack Pine, Red Pine, Lodgepole Pine, Scots Pine, Scotch Pine, Southern Yellow Pine, White Pine, Ponderosa Pine, Spruce, Cedar, Fir, or Redwood.
   c. Recycled pallets, typically containing a 50%-100% conifer fraction (depending on the pallets region of origin).
   d. Conifer wood combined with 50%-0% fibrous herbaceous lignocellulose, including corn stover, canola, flax fiber, wheat straw, barley straw, or fiberized cotton burrs.
   e. 100% hardwood or agricultural lignocellulose combined with up to 25% terpene. The lignocellulose may be white oak, birch, alder, poplar, walnut, maple, corn stover, hemp pith, kenaf pith, flax shive, canola, wheat straw, barley straw, soy straw, or cotton burrs. The terepene content may be derived from wood turpentine, pure gum turpentine (roughly 40:60 alpha-pinene: beta-pinene), or crude pine resin extractives.
3. The substrate of step 2 is combined with supplemental nutrition per the criteria of process step 3, example supplementation types and rates may include:
   a. 7% clear flour, 7% algae by-product
   b. 6% clear flour, 6% algae by-product, 2% Ca
   c. 7% clear flour, 2% Ca, 1% KOH
   d. 14% algae by-product
   e. Utilization of wheat bran in place of clear flour for a-d.
   f. Utilization of corn steep solids in place of clear flour and algae by-product for a-d.
4. The supplemented substrate of step 3 is heat processed per process step 4, some examples include:
   a. Pressure sterilized at 15 psi for 45-90 minutes.
   b. Pressure sterilized at 25 psi for 30 minutes.
   c. Pasteurized in a boiling water bath for 1-4 hours.
   d. Steam disinfected without pressurization for a period of 5-30 minutes.
5. The heat-processed substrate of step 4 is inoculated with spawn of the fungus species of step 1 per process step 5. The spawn may be composed of cereal grains, hardwood sawdust, or the substrate of process step 2.
6. The inoculated substrate of step 5 is filled into sterile bags or containers under aseptic conditions. The bags or containers have a porosity which allows for gas exchange and aerobic respiration.
7. The bags/containers of step 6 are incubated for a period of 5-14 days at a temperature appropriate for the fungus species of step 1 per process step 6. Incubation is discontinued once the fungus has expanded around and between all the particles creating a cohesive network of mycelial cells (i.e. the substrate is myceliated).
8. Per process step 7, the myceliated substrate of step 7 is removed from the bag/container and processed with a fluted roller to reduce the myceliated mass of particles to discreet particles with mycelium grown around and throughout each particle.
9. The remaining 90% fraction of the substrate of step 2 is combined with water to a moisture content of 55% per process step 8. At this stage, the substrate is not heat-processed to reduce bioburden or combined with supplemental nutrition.
10. Without necessity for aseptic process controls, the substrate of step 9 is combined with the discrete myceliated particles of step 8 per process step 9 at a rate of 10% myceliated particles and 90% substrate (dry mass basis).
11. The combined substrate and myceliated particles of step 10 are placed in a large, static mass per process step 10 within an environment that is (1) temperature controlled, (2) provides gas exchange to support aerobic respiration, and (3) maintains the moisture content of the substrate.
12. The static mass of substrate of step 11 is incubated for a period of 7 days per process step 10, at which point the fungus will have expanded from the myceliated particles of step 8 (10% fraction) and grown around and throughout the non-sterilized, non-supplemented particles of step 9 (90% fraction). During this incubation period, the aromatic monoterpenes will restrict the proliferation of contaminant mold, yeast, and bacteria species (ambient bioburden) while the fungus of step 1, which has been selected to tolerate the aromatic content, is able to expand and establish a "founder's effect" on the substrate thereby excluding contaminant species from any future growth.
13. The myceliated substrate of step 12 is reduced to discrete myceliated particles per step 8 and process step 7.
14. The discreet myceliated particles of step 13 are combined with supplemental nutrition per step 3 and process step 12.
15. The supplemented myceliated particles of step 14 are incubated per step 11 and process step 13 until the mycelium present on each particle expands creating a cohesive mass of substrate particles and mycelium. During this incubation phase, significant biomass accumulation is driven by the supplemental nutrition, which is made possible by the exclusion of competitor organisms per step 12.
16. The incubation phase of step 15 is continued until the total mass of substrate and mycelium is comprised of at least 10% mycelium on a dry mass basis per process step 14. If required, incubation may continue to reduce cellulose, hemicellulose, and/or lignin content of the substrate by enzymatic action of the fungus.
17. The myceliated substrate of 16 may be processed and used according to process step 15:
    a. The mycelium-substrate composite of step 16 may be applied as a low-density biomaterial.
    b. The mycelium-substrate composite of step 16 may be compressed under heat and pressure to create a high-density biomaterial.
    c. Steps 13, 15, and 16 may be repeated as desired to continue incubation for further biomass accumulation or hemicellulose/cellulose/lignin reduction.

Example 2: Impregnation of Lignocellulose Particles with Mycelium for Use as a Bioresin with Staged Nutritional Supplementation and Multiple Agitation Phases 1. Perform steps 1-13 of Example 1.
2. Select supplemental nutrition per process step 12, comprising one of a starch component, a lipid component, and a trace mineral component.
3. The lipid and mineral components of step 2 are combined with the discrete myceliated particles of Example 1 step 13.
4. Perform step 15 of Example 1.

5. Perform step 13 of Example 1.
6. The starch component of 2 is combined with the myceliated particles of step 5.
7. Perform step 17 of Example 1.

Example 3: Extended Incubation Periods to Effect Hemicellulose and Simple Sugar Reduction in Combination with Biomass Accumulation for Application as a Bioresin 1. Select a soft rot species per the criteria of process step 1. Species may include *Xylaria hypoxylon*, *Trichoderma* spp., *Kretzschmaria deusta*, *Xylaria filiformis*, *Pyrenomyxa picea*, *Daldinia grandis*, *Daldinia concentrica*, or *Hypoxylon* spp.
2. Perform steps 2-17 of Example 1.
3. Repeat step 17c until hemicellulose has been reduced by up to and exceeding 30% and simple sugars by up to and exceeding 70%.

Example 4: Extended Incubation Periods to Effect Cellulose and Lignin Reduction in Combination with Biomass Accumulation for Application as a Bioresin 1. Select a white rot species per the criteria of process step 1. Species may include *Trametes* spp., *Stereum* spp., *Trichaptum* spp., *Schizophyllum* spp., *Pleurotus* spp., *Ganoderma* spp., or *Phanerochaete* spp.
2. Perform steps 2-17 of Example 1.
3. Repeat step 17c until cellulose has been reduced by up to and exceeding 10% and lignin by up to and exceeding 25%.

Variations

Variations may be made to the process of the invention in accordance with the following.

1) Cultivation of Mycelium on Substrates Containing Conifer Wood

This process may be utilized in any context in which colonizing a solid substrate containing a >50% conifer fraction is required. Of particular interest are mycelium-based biomaterial applications within the engineered wood industry, which makes significant use of conifer wood for MDF, HDF, particleboard and chipboard manufacturing. In this case, mycelium is leveraged as a resin for binding together conifer wood particles as a direct replacement for urea-formaldehyde adhesive. This process makes it possible to utilize the conifer substrate supply chains already in place within the engineered wood industry, significantly increasing the ability to implement mycelium as a resin for engineered wood production.

2) Cultivation of Mycelium on Non-Conifer Terpene-Containing Substrates without Heat Sterilization/Pasteurization or Aseptic Control Manufacturing systems oriented toward solid-state cultivation of mycelium (mushroom cultivation, biomaterial production) largely require heat sterilization/pasteurization and aseptic control. These requirements are associated with significant infrastructural and processing costs. The process proposed here is appropriate for systems requiring cultivation of mycelium on solid substrate, and eliminates the need for equipment and methodologies for heat processing and maintaining aseptic cultivation conditions. This provides significant opportunity for reducing the set-up and operation costs of solid-state mycelium cultivation systems.

Process Steps

1) Select a fungus species according to the criteria of process step 1 described above with respect to FIG. 1.
2) Select a substrate according to the any combination of the following criteria:
   The substrate is comprised entirely of conifer wood
   The substrate is between 50% and 100% conifer wood blended with other plant matter
   The conifer fraction is comprised of a single wood species
   The conifer fraction is comprised of multiple wood species
   The substrate is a lignocellulose plant matter not derived from a conifer tree species, supplemented with terpene up to 25% of the dry mass of the substrate
   The substrate is a lignocellulose plant matter not derived from a conifer tree species, supplemented with the terpene-containing steam condensate of step 5 below
3) Combine the substrate of step 2 with supplemental nutrition according to the criteria of process step 12 described above with respect to FIG. 3.
4) Steam is injected into the substrate of step 2 for a period of 30 minutes to 4 hours in order to both sterilize the substrate in preparation for inoculation with the fungal species of step 1, and to remove terpene-containing extractives from the conifer fraction of the substrate.
   a. If an adequate extractive content remains in the conifer fraction to suppress bioburden growth (bacteria, yeast, mold) during incubation continue to step 7b.
   b. If an extractive content is inadequate for suppressing bioburden growth continue to step 7a.
5) During the steam injection of step 4, the steam is carried away from the substrate to remove terpene-containing extractives, which is condensed and isolated. This terpene-rich condensate can then be re-introduced into the myceliated substrate of step 8.
6) The substrate of step 2 is not heat processed to remove terpene-containing extractives or to sterilize/pasteurize per the following criteria:
   A fungus species of step 1 is selected which is tolerant of the ambient terpene content of the conifer fraction of step 2, which is demonstrated by an average mycelium expansion rate of at least 16 mm/day over a 10-day period on the given substrate.
7) The fungus species of step 1 is combined with the substrate of steps 2 and 3 (i.e. the substrate is inoculated).
   a. The inoculated substrate prepared per step 4b is incubated in aseptic conditions with environmental parameters appropriate for the fungus species selected until a desired quantity of mycelium has been cultivated.
   b. The inoculated substrate prepared per step 4a or step 6 is incubated without aseptic environmental control under conditions that best select for the growth of the fungus species of steps 1 or 6 over ambient bioburden (bacteria, yeast, mold) until a desired quantity of mycelium has been cultivated.
8) The substrate of steps 2 and 3 is completely myceliated with the fungus species of step 1 and processed as desired.
The following are specific examples of the above process.

Example 5: Production of Low- and High-Density Composites Utilizing a Substrate Composed of a Conifer—Hardwood Blend 1. The Basidiomycete species *Trametes elegans* is selected.
2. A wood substrate containing an 80:20 blend of conifer wood: hardwood particles is selected. The conifer fraction is composed of pine and spruce, the hardwood fraction is composed of maple, ash, and birch.

3. The substrate of step 2 is combined with 4% flour by-product, 4% algae by-product, 4% Ca, 0.5% potassium hydroxide, and hydrated to 55%-70% moisture 4. The supplemented substrate of step 3 is placed inside of a steaming vessel that may be pressure rated to at least 15 psi.

5. Steam is injected into the vessel of step 4 for a period of 2 hours. The substrate is turned/agitated periodically to ensure steam penetration. The vessel is not pressurized and the steam is vented from the vessel.

6. The steam exiting the vessel of step 5 is condensed and collected.

7. After steam processing (step 5) either a. or b. below is performed.
  a. If pressure rated, the vessel is pressurized to at least 15 psi for a period of at least 30 minutes, and then the substrate is allowed to cool to <100 F.
  b. The substrate is allowed to cool to <100 F without further heat processing.

8. The fungus species of step 1 is combined with the steam-processed substrate of step 7 (i.e. the substrate is inoculated).

9. The inoculated substrate of step 8 is placed in a container that prevents desiccation of the substrate and provides gas exchange for respiration.

10. The inoculated substrate of step 9 is incubated at 70-90 F for a period of 4-15 days, until the discrete particles of the substrate are adequately colonized/bound together by the mycelium of the fungus of step 1.

11. The steam condensate of step 6 is combined with the colonized substrate of step 10.

12. The colonized substrate impregnated with the steam condensate of step 11 is dried to moisture content of below 10%.

13. Perform a. or b. below
  a. The resultant material of steps 1-12 is utilized without further processing (typically <20 lb/ft3), for use in applications requiring a low-density composite.
  b. The resultant material of steps 1-12 is further processed via compression to a density of >20 lb/ft3, for use in applications requiring a high-density composite.

Example 6: Production of Low- and High-Density Composites Utilizing a Substrate Composed Entirely of Conifer Wood 1. Perform step 1 of example 5
2. A wood substrate entirely composed of conifer wood particles is selected. The conifer wood substrate may contain a single, or a multitude, of conifer wood species in any combination.

Example 7: Production of Low- and High-Density Composites Utilizing a Non-Sterile Cultivation Practice with Terpene-Containing Substrate 1. A fungus species is selected per process step 6.
2. One of the below substrates is selected.
  a. A lignocellulose substrate containing >50% conifer wood.
  b. A substrate composed entirely of conifer wood.
  c. Lignocellulose substrate containing no conifer wood, but supplemented with terpene or conifer wood extractives per process step 2.
3. Perform step 3 of example 5.

4. At least 200 ppm CuSO4 is combined with the water fraction used to hydrate the substrate.

5. The fungus of step 1 is combined with inexpensive agricultural waste, for example ground corn stalks (i.e. the agricultural waste is inoculated with the fungus). The inoculated agricultural waste is placed in environmental conditions appropriate for the fungus of step 1 and incubated until the agricultural waste is colonized with the mycelium of the fungus of step 1 (i.e. the substrate is myceliated). This myceliated agricultural waste will be used as spawn in step 6 below.

6. The supplemented substrate of steps 2 and 3 is combined with the spawn of step 4 at a rate of 1:10-1:1 (dry mass spawn: dry mass substrate).

7. The inoculated substrate of step 5 is incubated according to any combination of the below conditions to select for the growth of the fungus species of step 1 over that of bioburden (yeast, mold, bacteria) present in the substrate of step 2. Incubation is continued until the discrete particles of the substrate are adequately colonized/bound together by the mycelium of the fungus of step 1.
  a. Temperatures of 60-80 F, not to exceed 80 F
  b. Substrate moisture content not below 60% and not above 65%
  c. Substrate pH not below 6 and not above 7
  d. Gas exchange is restricted until initial ("guerilla") colonization of the fungus through the substrate is complete, in order to increase the efficacy of the aromatic terpenes on bioburden without retarding expansion of the mycelium of the fungus of step 1.
  e. Gas exchange is increased after initial ("guerilla") colonization in order to support efficient respiration of the fungus of step 1.

8. The colonized substrate is dried to moisture content of <10%.

9. Perform step 13 of Example 5.

Example 8: Fungus Species Selection

1. Generate candidate species per the criteria of process step 1, especially species considered common within a given environment. Example species include, but are not limited to:
  *Trametes elegans*
  *Trametes versicolor*
  *Trametes hirsuta*
  *Trametes gibbosa*
  *Stereum ostrea*
  *Stereum hirsutum*
  *Trichaptum biforme*
  *Xylaria hypoxylon*
  *Xylaria polymorpha*
  *Phellinus gilvus*
  *Schizophyllum commune*
  *Phanerochaete* sp.
  *Ganoderma* sp.
  *Trichoderma* sp
  *Pleurotus* sp.

2. Select and prepare the target substrate for colonization per process steps 2 and 3.

3. Fill 15×100 mm petri dishes with the substrate of step 2.

4. Transfer a small amount of mycelium to the center of a petri dish from step 3 (point of inoculation). Perform this process for each of the species identified in step 1.

5. Measure from the point of inoculation to the outer boundary of mycelium growth once daily to determine the linear expansion rate of each fungus species.

6. Use the data of step 5 and the criteria of process step 6 to select a fungus species for the target substrate of step 2.

Example 9: Substrate Compositions, Wood Species, and Nutritional Supplementation 1. Example substrate compositions (process step 2) may include, but are not limited to:
    Conifer wood combined with 50%-0% hardwood. The conifer fraction may be Jack Pine, Red Pine, Lodgepole pine, spruce, or fir. The hardwood fraction may be maple, birch, alder, ash, oak, or poplar.
    100% conifer wood. The composition can be one or more species in any combination, including Jack Pine, Red Pine, Lodgepole Pine, Scots Pine, Scotch Pine, Southern Yellow Pine, White Pine, Ponderosa Pine, Spruce, Cedar, Fir, and Redwood.
    Recycled pallets, typically containing a 50%-100% conifer fraction (depending on the pallets region of origin).
    Conifer wood combined with 50%-0% fibrous herbaceous lignocellulose, including corn stover, canola, flax fiber, wheat straw, barley straw, or fiberized cotton burrs.
    100% hardwood or agricultural lignocellulose combined with up to 25% terpene. The lignocellulose may be white oak, birch, alder, poplar, walnut, maple, corn stover, hemp pith, kenaf pith, flax shive, canola, wheat straw, barley straw, soy straw, or cotton burrs. The terepene content may be derived from wood turpentine, pure gum turpentine (roughly 40:60 alpha-pinene: beta-pinene), or crude pine resin extractives.

2. Example supplemental nutrition (process step 3) may include, but is not limited to (percentages by dry mass of substrate being supplemented):
    4%-7% clear flour, 4%-7% algae by-product, 2%-4% Ca, 0.5%-1% KOH
    6%-12% wheat bran, 2%-4% Ca, 0.5%-1% KOH
    4%-7% clear flour, 2%-4% Ca, 0%-1% KOH
    1%-7% wheat bran, 4%-7% algae by-product, 2%-4% Ca, 0.5%-1% KOH
    7%-14% algae by-product, 2%-4% Ca, 0.5%-1% KOH
    Brown rice flour, oat flour, or ground rye berries in place of clear flour/wheat bran for any of the above.

The invention thus provides an economically feasible process for solid-state cultivation of mycelium on a lignocellulose substrate and, particularly, a reduction in the cost of processing mycelium on a lignocellulose substrate.

The invention also provides a mycelium-based biomaterial for use in the engineered wood industry.

What is claimed is:

1. A process for solid-state cultivation of mycelium on a lignocellulose substrate comprising the steps of
    obtaining a lignocellulose substrate;
    combining a first fraction of said substrate with supplemental nutritional material at a ratio of up to 14% of the dry mass of said fraction and hydrating said fraction to a moisture content of from 40% to 70% by weight;
    heat processing the hydrated substrate fraction for a period of time sufficient to eliminate ambient bioburden and to maintain the hydrated substrate fraction in an aseptic condition;
    thereafter inoculating the hydrated substrate fraction with a predetermined fungus;
    thereafter incubating the inoculated substrate for a period of time to allow said fungus to grow hyphae and to allow said hyphae to form a network of interconnected mycelia cells through and around discrete particles of said substrate fraction to obtain a myceliated substrate;
    thereafter reducing the myceliated substrate into discrete particles;
    combining the remaining fraction of said substrate with water to obtain a moisture content of 40% to 70%;
    thereafter combining the moistened remaining fraction of said substrate with said discrete particles of myceliated substrate into a mass and incubating said mass for a period of time to allow said fungus in said discrete particles of myceliated substrate to grow hyphae and to allow said hyphae to form a network of interconnected mycelia cells through and around discrete particles of said remaining fraction of said substrate to obtain a second myceliated substrate;
    thereafter reducing the second myceliated substrate into discrete particles; and
    combining the discrete particles of said second myceliated substrate with supplemental nutritional material at a ratio of up to 14% of the dry mass of said second myceliated substrate and incubating said discrete particles and said nutritional material for a period of time to allow said fungus in said discrete particles of myceliated substrate to grow hyphae and to allow said hyphae to form a network of interconnected mycelia cells through and around discrete particles of said remaining fraction of said substrate to obtain a third myceliated substrate composed of at least 10% mycelium.

2. A process as set forth in claim 1 wherein said first fraction is up to 15% of said substrate.

3. A process as set forth in claim 1 wherein said lignocellulose substrate is comprised entirely of gymnosperm wood.

4. A process as set forth in claim 1 wherein said lignocellulose substrate is between 50% and 100% gymnosperm wood blended with other plant matter.

5. A process as set forth in claim 4 wherein the gymnosperm fraction is comprised of at least one wood species.

6. A process as set forth in claim 1 wherein said lignocellulose substrate has a native resin and monoterpene content.

7. A process as set forth in claim 6 has an additional terpene supplement.

8. A process as set forth in claim 1 wherein said lignocellulose substrate is a plant matter not derived from a gymnosperm tree species and is supplemented with terpene.

9. A process as set forth in claim 1 further comprising the step of compressing said third myceliated substrate to a density of greater than 20 pounds per cubic foot.

10. A process as set forth in claim 1 wherein said fungus is a soft rot species and said step of incubating said discrete particles of said second myceliated substrate and said nutritional material is conducted for a period of time to allow said fungus to reduce hemicellulose by up to 30% and simple sugars by up to at least 70%.

11. A process as set forth in claim 1 wherein said fungus is a white rot species and said step of incubating said discrete particles of said second myceliated substrate and said nutritional material is conducted for a period of time to allow said fungus to reduce cellulose by up to at least 10% and lignin by up to at least 25%.

12. A process as set forth in claim 1 wherein said fungus is one of a saprophytic white rot, brown rot, or soft rot and is characterized in being tolerant of the monoterpene content associated with said substrate and in producing structural cellular components comprised of thick-walled cells.

13. A process as set forth in claim 12 wherein said substrate contains up to 25% resin (w:w).

14. A process as set forth in claim 1 further comprising the steps of
reducing the third myceliated substrate into discrete particles; and
combining the discrete particles of said third myceliated substrate with supplemental nutritional material at a ratio of up to 14% of the dry mass of said third myceliated substrate and incubating said discrete particles and said nutritional material for a period of time sufficient for the total dry mass of said third myceliated substrate to be composed of at least 10% fungal biomass.

* * * * *